US00PP32591P2

(12) United States Plant Patent
Hansen

(10) Patent No.: US PP32,591 P2
(45) Date of Patent: Dec. 8, 2020

(54) ***DIANTHUS* PLANT NAMED 'GOODY GUMDROPS'**

(50) Latin Name: ***Dianthus* hybrid**
Varietal Denomination: Goody Gumdrops

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/873,017

(22) Filed: Jan. 15, 2020

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./273, 276, 277
CPC ..... A01H 5/02; A01H 5/0233; A01H 5/00; A01H 6/30; A01H 6/305; A01H 6/1424
See application file for complete search history.

(56) References Cited

U.S. PATENT DOCUMENTS

PP14,919 P2 * 6/2004 Whetman ..... A01H 6/305 Plt./272

OTHER PUBLICATIONS

Aris Green Leaf Plants *Dianthus* Industry Leader in *Dianthus* Production 2019, retrieved on Jul. 20, 2020, retrieved from the Internet at http://www.glplants.com/system/cms/files/files/000/000/952/original/SS-19024-GLP_Dianthus_WEB-SEQ.pdf, pp. 1-16. (Year: 2019).*

The Plant Connection A Division of BFG Supply Co. 2020, retrieved on Jul. 20, 2020, retrieved from the Internet at https://www.bfgsupply.com/_CE/pagecontent/Documents/Plant%20Connection%202020/2020%20Green%20Leaf%20Perennial%20Product%20list.pdf, pp. 1-5,12,45. (Year: 2020).*

* cited by examiner

*Primary Examiner* — June Hwu

(57) ABSTRACT

A new and unique plant cultivar of perennial carnation or pinks, *Dianthus* plant named 'Goody Gumdrops' with numerous, medium-sized, semi-double, lightly-fragrant flowers producing a rounded face. The numerous stems have up to 3 flowers per stem. Petals have medium depth teeth along margin. Petals of young flower begin fuchsia-pink with red bar upon opening and mature to a light purple-pink. The habit is compact with long, thin, heavily-glaucous, blue-green foliage.

1 Drawing Sheet

Botanical denomination: *Dianthus* hybrid.
Cultivar designation: 'Goody Gumdrops'.

STATEMENT REGARDING PRIOR DISCLOSURES UNDER 37 CFR 1.77(B)(6)

The first non-enabling disclosure of the claimed plant was made by Walters Gardens, Inc. on Feb. 1, 2019 in the form of a website brief description and photograph followed by a short description and photograph in the "Walters Gardens 19-20 Catalog" by Walters Gardens, Inc. The first sales of the claimed plant was on Jul. 8, 2019 by Walters Gardens, Inc. Walters Gardens, Inc. obtained the new plant and information about the new plant directly from the inventor. No plants of *Dianthus* 'Goody Gumdrops' have been sold, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct cultivar of carnation or pinks from the genus *Dianthus* and given the cultivar name 'Goody Gumdrops'. The new plant was the result of an intentional cross on May 14, 2012 under the direction of the inventor between 'Devon Esther' U.S. Plant Pat. No. 18,222 as the female or seed parent and 'Devon PP' U.S. Plant Pat. No. 14,919 as the male or pollen parent. The cross was harvested and sown in the late fall of 2012. The new hybrid was first selected from trials at a wholesale perennial nursery in Zeeland, Mich. during the summer of 2014 as a single seedling clone and given the breeder code number 12-22-1 later in the evaluation processes. *Dianthus* 'Goody Gumdrops' has been asexually propagated at the same nursery in Zeeland, Mich. since 2014 using traditional shoot tip cutting procedures and later sterile shoot-tip tissue culture and found to reproduce plants that are identical and exhibit all the characteristics of the original plant.

SUMMARY OF THE INVENTION

*Dianthus* 'Goody Gumdrops' has not been evaluated under all possible environmental conditions. The phenotype may vary with variations in environment including: growing temperature, available sunlight, nutrients, water, etc. without a change in the genotype of the plant The new plant can be most closely compared with: 'Appleblossom Burst' U.S. Plant Pat. No. 31,454, 'Cute as a Button' U.S. Plant Pat. No. 31,453, 'Devon Flavia' U.S. Plant Pat. No. 15,903, 'Sweetie Pie' U.S. Plant Pat. No. 27,989 and the parents 'Devon Esther' and 'Tickled Pink'. 'Appleblossom Burst' has a greater color change in the flowers becoming near white to pale pink and denser in habit. 'Cute as a Button' has lighter reddish pink flower on a plant that is more compact. 'Devon Flavia' has a slightly taller habit with more flowers per stem and more petals per flower that are light reddish-purple. 'Sweetie Pie' has more branching and more flowers per plant and the petals of a more purplish-red colored without a dark red bar. 'Devon Esther' has flowers that are more reddish-purple on more vigorous plants. 'Tickled Pink' has flowers that are fuchsia in color and lack the dark red bar.

*Dianthus* 'Goody Gumdrops' is distinct from its parents and all other *Dianthus* known to the applicant in the following combined traits:

1. Semi-double flowers opening up with a full rounded face.
2. Petals open a fuchsia-pink with red bar near the base of the petal limb.
3. Petal color lightens with age to a light purple-pink;
4. Petal margin irregularly toothed to medium depth;
5. Multiple flowers per stiff, upright peduncle;
6. Medium flower size producing a lightly-sweet spicy fragrance;
7. Compact habit and dense, heavily-glaucous blue-green foliage.

BRIEF DESCRIPTION OF THE DRAWINGS

The photographs of 'Goody Gumdrops' are of a two-year-old plant grown in full-sun trial garden in Zeeland, Mich. showing the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
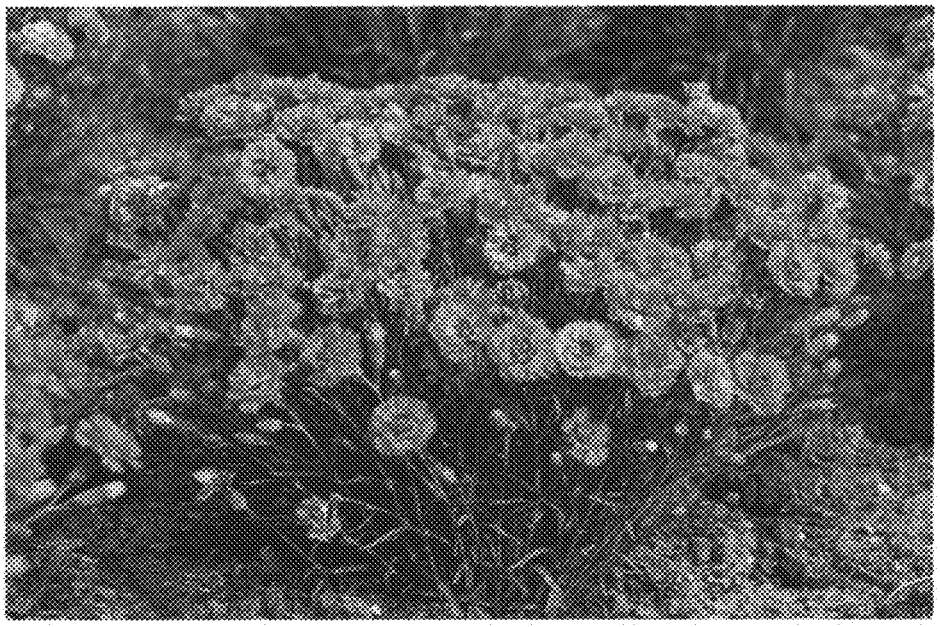
FIG. 1 shows the habit of the plant in mid-season flowering.
Figure 2:
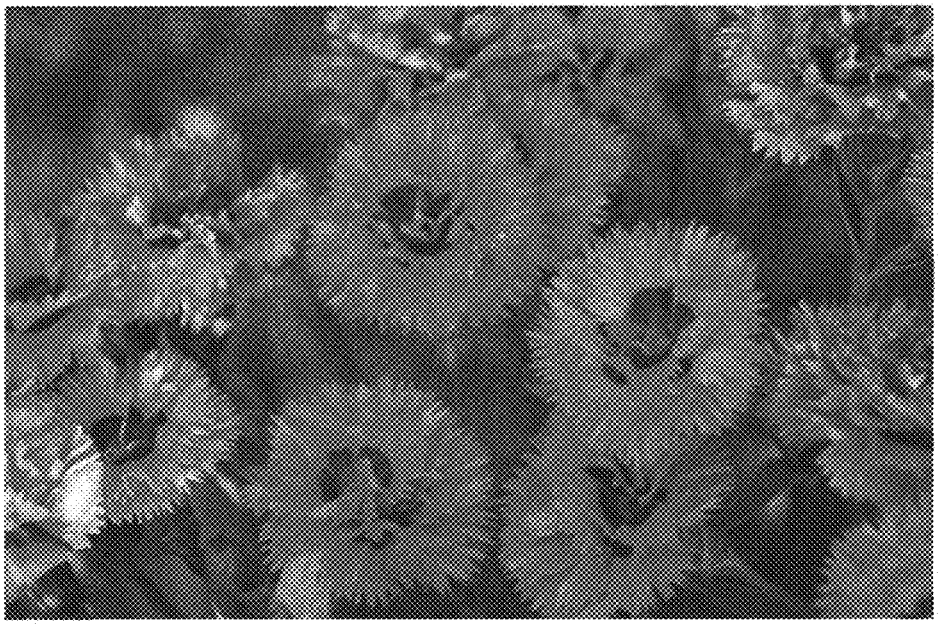
FIG. 2 shows a close-up of the flowers and bud.

The following detailed description of the new plant is based on observations of two-year-old plants in a partially shaded greenhouse at a nursery in Zeeland, Mich. with supplemental watering, light additions of fertilizer and free of other plant growth regulators. All color usage is in accordance with the 2015 edition of The Royal Horticultural Colour Chart except where common dictionary terms are used.

Botanical classification: *Dianthus* hybrid;

Parentage: The female or seed parent is 'Devon Esther'; the male or pollen parent is 'Devon PP';

Plant habit: Caespitose, herbaceous, evergreen, winter-hardy perennial; stems and peduncles highly branched, mostly erect stems to slightly arching; height of foliage about 12.0 cm and about 50.0 cm across; height in flower is about 22.0 cm;

*Root system*.—Fine, fibrous; color nearest RHS 155D.

*Vigor*.—Good, spring planted plugs finish in 3.8 liter pots in seven to eight weeks.

Foliage:

*Leaf type*.—Simple, linear, opposite, decussate, sessile, glabrous, heavily glaucous both adaxial and abaxial; margin entire to microscopically serrulate; acute narrowly apex; base truncate, decurrent, clasping; no fragrance detected; very weakly recurved distally.

*Leaf dimensions*.—To about 7.8 cm long and about 7.0 mm wide, average about 6.5 cm long and 5.0 mm wide.

*Leaf color*.—Young expanding leaves adaxial and abaxial blend between RHS 122A and RHS N138A; mature abaxial and adaxial blend between RHS 122A and RHS N138A.

*Venation*.—Not pronounced; obscurely pinnate, coloration same as that of leaf top and bottom.

Stems: About 76 per plant; upright; cylindrical, hollow; glabrous; heavily-glaucous; solid; branching in upper nodes;

*Stem size*.—About 19.0 cm long to peduncle and about 2.5 mm wide at base.

*Stem color*.—Nearest RHS 122A.

*Branching*.—Numerous; typically alternate from lower nodes; about 5 per main stem and about 300 per plant; branch size average about 3.5 cm long and 1.0 mm diameter at time of initial flowering.

*Nodes*.—About 3.5 mm across; color nearest RHS 142D.

*Internodes*.—About 9 per stem before peduncle; average about 2.1 cm apart depending on growing temperature, shorter in cooler conditions.

Inflorescence: Flowering in the upper 4.0 cm and to about 8.8 cm across; with an average of two flowers per inflorescence;

Flower:

*Type*.—Terminal, cymose; perfect; salverform; actinomophic; semi-double.

*Attitude*.—Uptight to slightly outward around perimeter of plant.

*Dimension*.—About 3.7 cm across and extending about 3.1 cm above base of calyx tube and 7.2 mm wide at apex of calyx.

*Flowers per stem*.—Up to 3, average 2.

*Pedicel*.—Glaucous, glabrous, cylindrical, stiff; primarily upright.

*Pedicel size*.—Variable; terminal flower to about 3.5 mm long and about 2.0 mm diameter; other flowers average about 8.0 mm long and 1.0 mm diameter.

*Pedicel color*.—Nearest RHS 122A.

*Flower bud*.—Slowly opening; glabrous; glaucous; with calyx still closed: cylindrical with attenuate base and rounded apex; about 21.0 mm long and 7.0 mm across at distal fusion point of sepals.

*Flower bud color*.—With petals extended beyond calyx petal portion nearest RHS 64A; calyx proximally nearest RHS 144D and distally nearest RHS 138B.

*Flower period*.—Beginning late spring and continuing for about three weeks, repeating in early fall.

*Flower fragrance*.—Light, sweet spicy, clove-like.

*Flower lasting quality*.—Individually about seven to ten days on or cut from plant.

*Corolla profile*.—Lower part flat; upper portion flat convex to convex.

*Petals*.—Glabrous adaxial and abaxial; up to about petals 25 per flower, average about 22.3; consisting of a rounded blade or limb and a claw; limb and claw combined are flabellate; limb apex and margin moderately dentate; with single, dark, adaxial band about 2 to 3 mm wide having a pointed center; limb bent outwardly on outer petals in distal 18.0 mm to nearly a ninety degree angle and inner petals straight creating a rounded face; persistent; without stripes or macula.

*Petal dimensions*.—Limb to about 18.0 mm across; average about 16.0 mm across; claw tapering to attenuate base of about 1.0 mm across; whole petal to about 33.0 mm long, average about 30.5 mm long.

*Petal color*.—Young adaxial claw nearest RHS 145C, young adaxial limb base nearest RHS NN155D with bar stretching at base of limb between RHS 61A and RHS 71A; young abaxial claw nearest RHS 145C, young abaxial limb base nearest RHS 155B, distal blade lighter or more white than RHS NN74B; mature adaxial claw nearest RHS 145C with midrib nearest RHS 145B, mature adaxial limb base and proximal center nearest RHS NN155D, dark band between RHS 61A and RHS 71A and distal blade nearest RHS N74D; mature abaxial claw nearest RHS 145C with center midrib nearest RHS 145B mature abaxial limb base nearest RHS 75B and distally nearest RHS 75A.

*Calyx*.—Terete to campanulate; to about 17.0 mm long and 7.0 mm diameter at apex.

*Sepals*.—Five; acute apex and fused in basal 14.0 mm forming five-toothed calyx tube; glabrous; glaucous abaxial; margins entire to micro-ciliolate.

*Sepal size*.—Individually about 17.0 mm long and about 3.0 mm across at distal fusion.

*Sepal color*.—Adaxial margin translucent to nearest RHS 158D, distally nearest RHS 147C, proximally nearest RHS 145C; abaxial margin translucent to nearest RHS 157C, mid-portion between RHS 138B and RHS 146A with translucent margin nearest RHS 158D, base nearest RHS 146D; anthocyanin pigment not present in visible amounts.

*Peduncle*.—Glabrous; glaucous; hollow, cylindrical; stiff; about 10.0 cm long and about 2.5 mm diameter at base; attitude mostly upright to slightly arching.

*Peduncle color*.—Blend nearest RHS 122A with glaucous bloom.

*Epicalyx*.—Two pairs subtending each flower; both pairs adpressed; opposite, glaucous, glabrous; sessile, margin entire and translucent in outer 1.0 mm; deltoid; inner pair with very short acute apex and truncate base, 9.0 mm long and about 6.0 mm across near middle; outer pair with very short narrowly acute apex, truncate base, about 7.0 mm long and about 5.0 mm wide.

*Epicalyx color*.—Both pairs adaxial and abaxial margin nearest RHS 158C and remaining epicalyx nearest RHS 141A; no anthocyanin pigment noted.

*Androecium*.—Typically about 7; not fully developed. Filaments: straight to about 10 mm long and 0.5 mm diameter; color nearest RHS NN155A. Anther: rudimentary; acute apex and auriculate base; basifixed; about 1.5 mm long and 0.5 mm wide and 0.2 mm thick; color nearest RHS NN155A. Pollen: not observed.

*Gynoecium*.—Single; to about 27.0 mm long. Style: bifurcate or trifurcate just above ovary; arcuate in distal 3 mm to 270°; slightly applanate adaxial to abaxial; shoulder absent; to 18.0 mm long; straightened to 20 mm long and 0.7 mm across; not generally exserted beyond petals; color nearest RHS NN155B. Stigma: slightly flattened abaxial to adaxial; puberulent along adaxial surface; about 7.0 mm long and 0.7 mm wide; color nearest RHS N155B abaxial and adaxial nearest RHS 76C. Ovary: superior; obellipsoidal (almost ellipsoidal with distal end slightly larger) to fusiform, rounded acute apex and base; very slightly longitudinally fluted; about 8.0 mm long and 4.0 mm wide in center; color distally nearest RHS 145B and proximally nearest RHS 146D.

Fruit: Not observed;

Disease resistance: The new plant is resistance to center die out from fungus or high temperatures. The plant grows best with adequate moisture and well-drained soil, but is able to tolerate some drought once established. Hardiness at least from USDA zone 4 through zone 9.

It is claimed:

1. A new and distinct *Dianthus* plant named 'Goody Gumdrops' essentially as herein described and illustrated.

* * * * *